Figure 1:
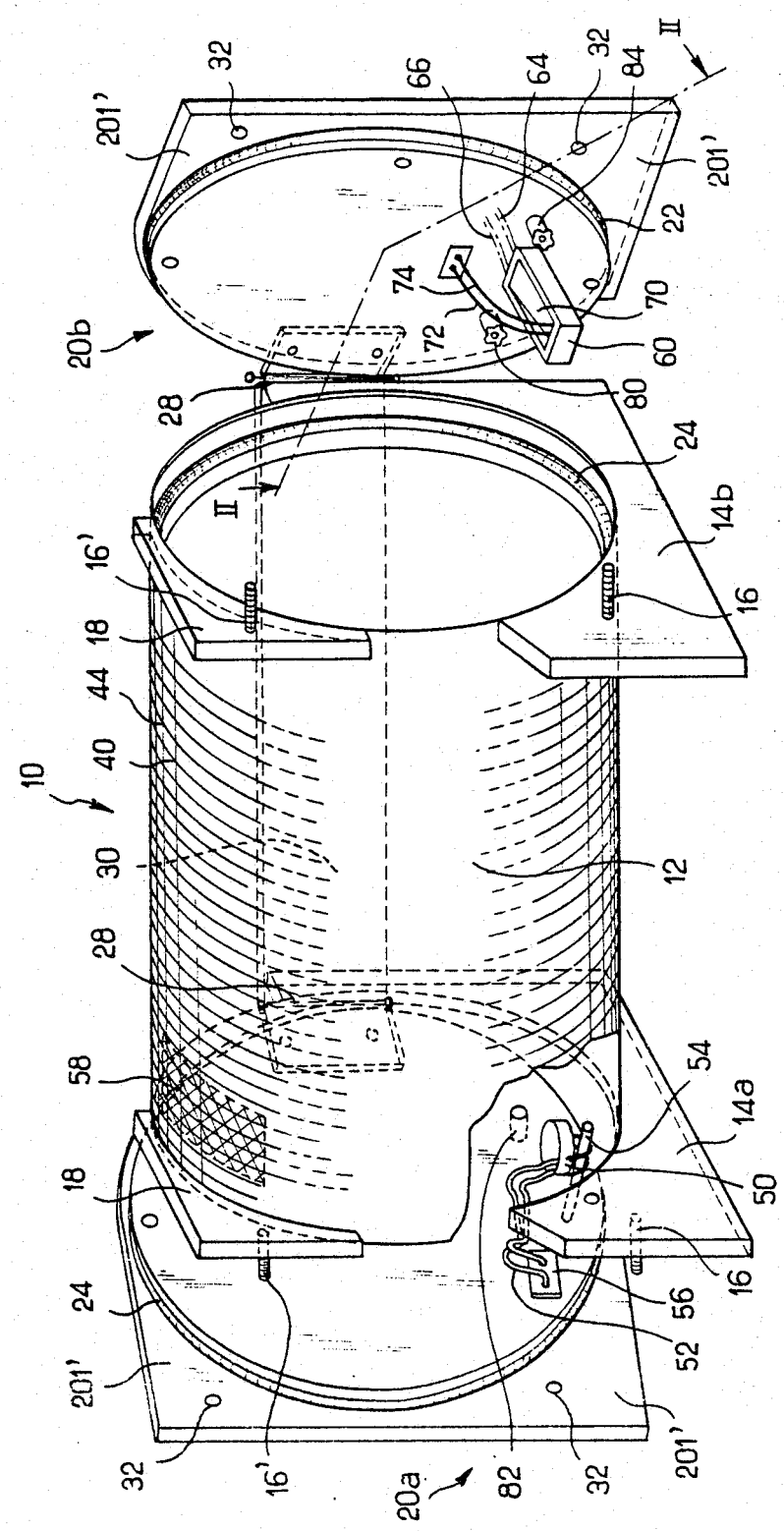

United States Patent [19]
Rio et al.

[11] Patent Number: 4,789,524
[45] Date of Patent: Dec. 6, 1988

[54] DEVICE FOR MEASUREMENT OF CORROSIVENESS OF SMOKE

[76] Inventors: Pierre Rio, 8 rue Noël; Jacky Gautier, AD 222, rue d'Anjou, Ker Uhel, both of 22300 Lannion; Hubert Ubertal, Kernu, Louannec, 22700 Perros-Guirec, all of France

[21] Appl. No.: 75,171

[22] Filed: Jul. 20, 1987

[30] Foreign Application Priority Data

Jul. 22, 1986 [FR] France ............... 86 10607

[51] Int. Cl.⁴ ............ G01N 17/00; B01L 11/00; B01L 3/00
[52] U.S. Cl. .................. 422/53; 422/101; 422/102
[58] Field of Search ............ 422/53, 99, 101–104; 73/86, 53, 865.6; 436/6

[56] References Cited

U.S. PATENT DOCUMENTS

Re. 25,932 12/1965 Neffenger ............... 436/6
3,163,497 12/1964 Gill ............... 436/6
3,259,466 7/1966 Jacks, Jr. ............... 436/6
3,957,440 5/1976 Aussieker ............... 23/253 C
4,600,695 7/1986 Cummings et al. ............... 436/2
4,683,035 7/1987 Hunt et al. ............... 436/6

FOREIGN PATENT DOCUMENTS 1147412 11/1963 Fed. Rep. of Germany .
1162107 1/1964 Fed. Rep. of Germany .
2317530 11/1973 Fed. Rep. of Germany ........ 422/53
2361709 6/1975 Fed. Rep. of Germany .
2537429 3/1977 Fed. Rep. of Germany ........ 422/53
52-72287 6/1977 Japan ............... 422/53
1356023 6/1974 United Kingdom .

OTHER PUBLICATIONS

Centre National d'Etudes des Telecommunications, "Presentation de l'essai Corrosivite mis au point au CNET-LAB-SERV/ENV".
Methodes D'Essais, Comportement Au Feu, "Determination de la corrosivite des fumees".

Primary Examiner—Barry S. Richman
Assistant Examiner—T. J. Wallen
Attorney, Agent, or Firm—Fulbright & Jaworski

[57] ABSTRACT

A device for measuring the corrosiveness of smoke, comprising a chamber, means for creating in the chamber an atmosphere of air of predetermined humitidy, heating means for heating the said atmosphere and walls of the chamber to a predetermined temperature, means for causing the combustion of a sample of material in the chamber, water circulation cooling means for condensing the smoke and products of pyrolysis generated by the said combustion onto a resistive metallic element exposed inside the chamber, the measurement of the corrosiveness of the smoke being carried out by measuring the variation in electrical resistance of the said element. The chamber comprises: a cylinder of methyl polymethacrylate open at its two ends; two thermally insulating end doors, constituted by an assembly of methyl polymethacrylate panels separated by interstitial air, and means for thermal insulation and gas-tightness between the doors and the cylinder, and heating means comprising a resistive metallic wire wound in a helix on the external periphery of the cylinder.

3 Claims, 2 Drawing Sheets

DEVICE FOR MEASUREMENT OF CORROSIVENESS OF SMOKE

FIELD OF THE INVENTION

The present invention relates in a general manner to devices for measurement of corrosiveness and more particularly a device intended for measurement of the corrosive effects of combustion of certain plastic materials on metals.

BACKGROUND OF THE INVENTION

On burning or the like, for example in an automatic telephone exchange, plastic materials burn releasing fumes and products of pyrolysis containing particles in suspension and corrosive gases. When these hot gases come into contact with colder parts, of which the temperature is less than their dew point, and in particular with metallic conductors, they are deposited by condensation on these conductors. In numerous cases, these deposits contain elements such as halogen ions, acids, bases, which corrode the metals by a chemical process, and indeed an electro-chemical process where there exists electric voltage.

A device for measuring the corrosiveness of smoke permits then determination, by successive trials, of the plastic materials of which the combustion will cause the least damage to conductive parts.

There is already known in the prior art, from a number of publications of the applicants, a device for measuring corrosiveness of smoke comprising a chamber, means for creating in the chamber an atmosphere of air of predetermined humidity, heating means for heating the said atmosphere and the walls of the chamber to a predetermined temperature, means for causing combustion of the sample of material in the chamber, water circulation cooling means for condensing the smoke and products of pyrolysis generated nn the said combustion on a resistive metallic element exposed inside the chamber, the measurement of the corrosiveness of the smoke being carried out by measuring the variation of electrical resistance of the said element.

For allowing condensation of the smoke on a colder measurement test piece, constituted by the resistive element, the atmosphere inside the chamber should be maintained at a temperature of the order of 50°, which is provided, in the prior art, by using as a heating means a climatic chamber in which the device is placed.

However, an inconvenience of this solution is that it is then impossible to observe the behaviour of the device, and particularly the manner in which the combustion, the condensation of the combustion products on the test piece, and the attack of the metal proceeds.

In this regard, with such a known device, it is necessary in the embodiment of the chamber to find a difficult compromise between good resistance to aggressive gases, so as not to alter the characteristics of the atmosphere inside the chamber, and a relative thermal transparency. With this in mind, the chamber of the prior art device comprises a Pyrex (Registered trade mark) glass cylinder covered internally with a coating resistant to aggressive gases, but not transparent and threaded end walls of methyl polymethacrylate across which pass various lines associated with the means for carrying out the measurement.

Further, a a major parameter which must be controlled for ensuring reproducability of the measurement of the corrosion is the relative humidity inside the chamber. This humidity is affected by any loss of gas-tightness which leads, by re-establishment of equilibrium of the partial pressures between the internal humid atmosphere and the dry atmosphere of the climatic chamber, to a notable diminution of the proportion of water molecules involved in the condensation.

Further, the condensation of the combustion products on the test piece is disturbed by undesirable cooling of certain parts of the walls of the chamber, and an ill-determined proportion of the humid smoke present in the chamber is then condensed on these parts instead of condensing on the test piece.

THE INVENTION

The present invention has the object of proposing a device for measuring corrosiveness of smoke in which this relative humidity is correctly controlled and the cold points are eliminated, in a manner to be able to carry out repeatable and reproducable measurements. Another object of the invention is to propose a device in which the different phases of operation can be easily observed.

For this, the device of the present invention is characterised in that the chamber comprises: a cylinder of methyl polymethacrylate open at its two ends; two thermally insulating end doors, constituted of an assembly of methyl polymethacrylate panels separated by interstitial air, and thermally insulating and gas-tight means between the doors and the cylinder; and in that the heating means comprises a resistive metallic wire helically wound on the external periphery of the cylinder.

THE DRAWINGS

Figure 2:
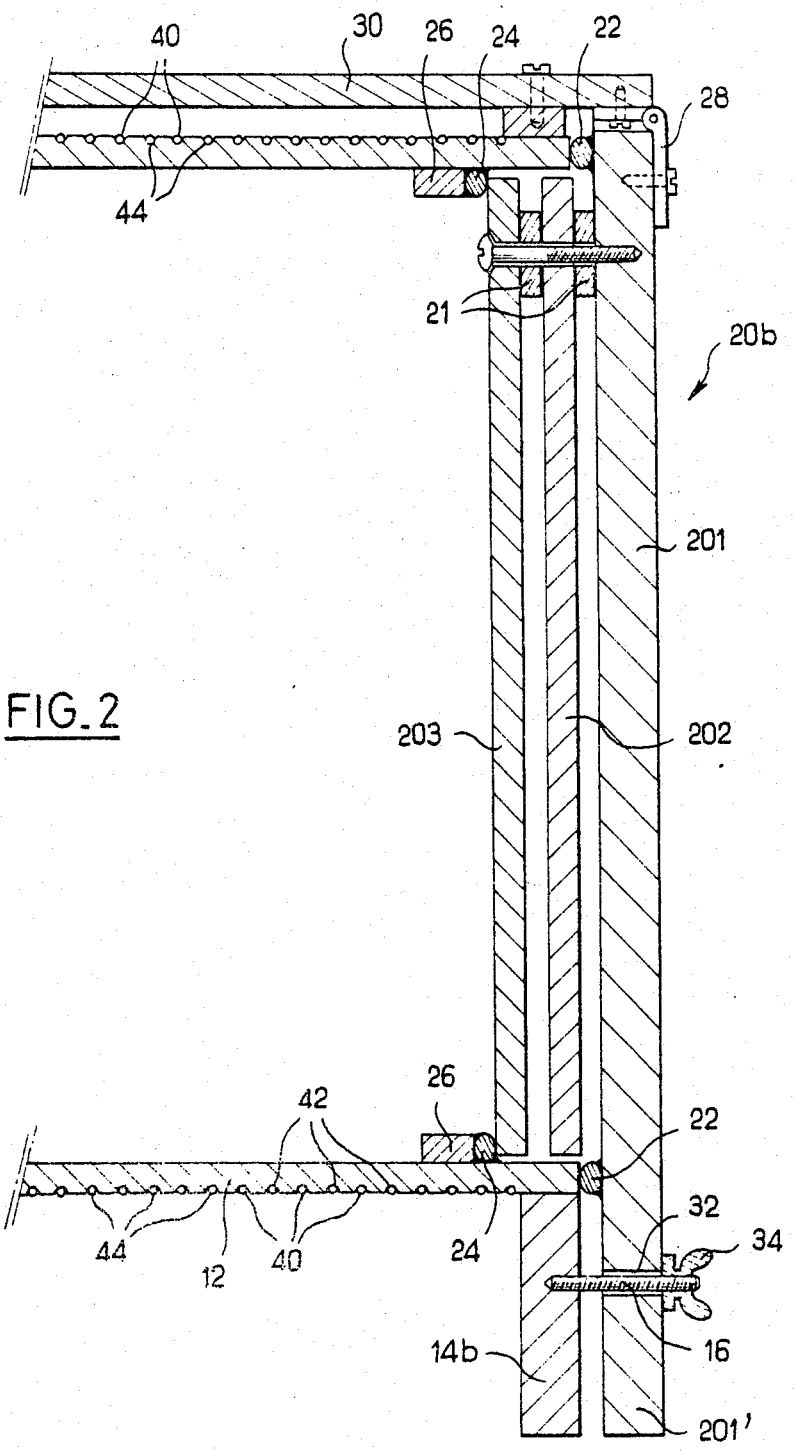

Other aspects and advantages of the present invention will better appear from reading the following detailed description of a preferred embodiment, given by way of example and with reference to the accompanying drawings, in which:

FIG. 1 is a perspective view of the entire device according to the invention, and FIG. 2 is a partial cross-section of a view on the line II—II of FIG. 1.

PREFERRED EMBODIMENT OF THE INVENTION

The device according to the invention comprises firstly a chamber 10 constituted by a horizontal axis cylinder 12 of transparent methyl polymethacrylate. The cylinder is supported at its two ends by two feet 14a, 14b on which it is preferably adhesively secured. Each foot has a threaded rod 16 extending outwardly, and identical threaded rods 16' are also provided above the rods 16 in plates 18 adhesively secured at the edge of the openings of the cylinder in vertical alignment with the feet.

The cylinder is closed at its two ends by two pivoted doors 20a, 20b each constituted of three transparent methyl polymethacrylate panels separated from each other by air spaces, in order to ensure appropriate thermal insulation. More precisely, and as FIG. 2 shows, each door, of circular shape, comprises a relatively thick base external panel 201, an intermediary panel 202 and an inside panel 203. The panels are held at a predetermined spacing from each other by appropriate spacers 21. The outside panel 201 is greater than the external cross-section of the cylinder 12 and carries an O-ring 22, for example adhesively secured, able to come into contact with the associated edge of the cylinder when the door is closed. The intermediary and inside panels have a slightly smaller diameter than the internal diameter of the cylinder and, in a closed position, the inside panel comes into abutment against a second O-ring 24 held in an axial direction by an axial abutment element 26 of annular shape, in methyl polymethacrylate.

It will be noted that methyl polymethacrylate is advantageously chosen for the construction of the chamber because of its excellent resistance to a large range of corrosive agents and because it exists in transparent form.

A hinge 28 is mounted between a frame member 30 extending horizontally behind the cylinder, for example fixed onto a rear upper extension of each of the support feet 16a,16b, and the associated external panel 201. Further holes 32 are provided opposite the screwed rods 16,16' in radial extensions 201' of the external panel 201 of each door, for receiving these latter. In the closed position, wing nuts 34 are engaged on the screwed rods 16,16' for tightening the associated door and compressing the O-rings 22,24, as shown in FIG. 2. It can be noted that the O-rings 22,24 serve to insulate the air spaces situated between the panels of the doors with respect to the exterior and with respect to the internal atmosphere of the chamber, respectively. The chamber is thus perfectly gas-tight, with optimum thermal insulation.

In accordance with the invention, the chamber is provided with controlled heating means which comprise firstly a heating element 40 in the form of an electrically resistive wire, preferably copper, helically wound in a complementary groove 42 provided on the external periphery of the cylinder 12, throughout the length of this. The wire 40 will be fed from an appropriate electric generator.

In addition, an element forming a temperature probe has the form of a second copper wire 44 helically extending in a groove 46 parallel to the first wire 40. Variations of the temperature of this second wire 44 cause corresponding variations of its resistance, and one can easily conceive with the heating element and the detection element a temperature regulation permitting maintenance of the temperature inside the chamber at a chosen value, preferably between ambient temperature and 70° C. It can be noted that the heating means having the construction described above also have the effect of heating the walls of the chamber to a relatively uniform temperature of predetermined value, with results explained below.

The device further comprises means for generating smoke by burning a sample of material of which the corrosiveness of its smoke is to be measured. More precisely, there is provided a circular silica dish 50, its material being chosen for its excellent resistance to thermal shocks, at the bottom of which is wound a spiral resistance 52 constituted by a nickel-chrome alloy wire sheathed with material known under the name "Inconel" (Registered trade mark), chosen for its good resistance to corrosion. The dish 50 is mounted on the inside face of the door 20a, in the bottom of this, by means of a support rod 54, for example of stainless steel. The two cold ends of the resistance 52 are connected to a connector 56 traversing the door and permitting connection of the said resistance to an appropriate current generator (not shown).

The sample of plastic material submitted to test is advantageously presented in the form of granules, of which the quantity predetermined with precision will be placed in the dish 50. Passing electric current through the resistance 52 will then be carried out for providing in the dish a temperature sufficient for causing the pyrolysis of the material.

There can be provided, in the region of the chamber where the burning is carried out, an internal covering of "Teflon" (Registered trade mark) indicated at 58, intended to protect the walls of the chamber during combustion.

A device for condensation of smoke and generated pyrolysic products of combustion by the mentioned burning is mounted in the lower region of the opposite door 20b. This device comprises a support 60 of methyl polymethacrylate having the form of a hollow parallelepiped in which is embedded a radiator formed of a copper plate (not visible), leaving however between the bottom of the support and the radiatior a cavity. Cooling water is circulated in this cavity, by feed and return ducts, respectively 64 and 66, traversing the door 20b.

A measurement test piece, schematically shown at 70, is placed in the support 60 in a manner to be in thermal contact with the radiatior mentioned above. Silicone grease can be used for this, for example.

The test piece will advantageously have the form of a resistive electric circuit carried by a support and preferably obtained by the engraving technique well known in the field of printed circuits. It comprises a thin strip of copper in serpentine formation on the support and terminating in two larger conductive surfaces which permit connection of the test piece, by two conductors 72,74 traversing the door 20b, to apparatus for measurement of electric resistance (not shown).

Finally, there is provided means for generating inside the chamber an atmosphere having well determined humidity. These means comprise a dry air inlet duct 80 and a return air duct 82 respectively traversing the doors 20b and 20a. These ducts will preferably be equipped with stopcocks permitting interruption of the circulation of air at a predetermined instant. These means further comprise a third duct 84, traversing the door 20b close to the duct 80, this third duct being normally closed by a membrane (not shown).

Obtaining the desired degree of humidity is carried out by firstly circulating in the chamber dry air, in order to determine a base point of the relative humidity of the inside of this, for example at less than 5%. A predetermined quantity of water is then introduced inside the chamber across the membrane, for example by means of a syringe, for obtaining the desired degree of relative humidity before burning of the sample.

The above device functions in the following manner: first there is placed in the silica dish 50, in contact with the resistance 52, a predetermined quantity of sample of which the smoke is to be analysed, and at the same time a new test piece is placed in the support 60. The doors 20a and 20b are then reclosed and the heating means and the means for generating humid air are operated for obtaining inside the chamber an atmosphere of given temperature and humidity. The sample is then burned by supplying current to the resistance 52, and the smoke and products of pyrolysis thus formed are condensed by natural convection on the cold surface of the test piece, this condensation being rendered possible by the establishment of a relatively high hygrometry. It can be noted in this regard that the condensation is carried out with a very good selectivity due in the main to the walls of the chamber being maintained by the heating means at a determined temperature, of the order of 50°, avoiding condensation on these walls. The value of the resistance of the test piece 70 is measured and then periodically recorded, and the significance of the corrosive effect of the smoke and products of pyrolysis on the copper is deduced.

In practice, this device facilitates the choice of most appropriate plastic materials, particularly in telephone exchanges, for minimising the degradation of conductor circuits in the case of a fire.

The device described above, and particularly the structure of the chamber and its integral controlled heating means, is advantageous in that it permits obtaining in a repeatable and reproducable manner the condensation of smoke and products of pyrolysis obtained by combustion of plastic materials. More particularly, the invention permits a good control of the thermal cycle applied to the device, as well as a good selectivity of the condensation, particularly thanks to high homogeneity of the temperature of the different walls of the chamber, creating no undesirable condensation of the cold parts other than the test piece.

Further, the structure of the invention, in avoiding the vagaries which have been due in the prior art to the use of a climatic chamber, permits observation of the combustion, condensation and corrosion phenomena, which are, apart from the measurement as such, elements determining the choice of the plastic materials.

Of course, the present invention is not limited to the embodiment described above and shown in the drawings, but the man skilled in the art will be able to incorporate variants and modifications without departing from its scope.

We claim:

1. In a device for measurement of corrosiveness of smoke, comprising a chamber having walls, means for creating inside said chamber an atmosphere of air of predetermined humidity, heating means for heating said atmosphere and said walls of said chamber to a predetermined temperature, means for causing combustion of a sample of material in said chamber, water circulation cooling means for condensing smoke and products of pyrolysis generated by said combustion onto an electrically resistive metallic element exposed inside said chamber, measurement of corrosiveness of said smoke being carried out by measuring variation in electrical resistance of said element, the improvement comprising:

said chamber walls being a methyl polymethacrylate cylinder having first and second open ends and having external periphery;

a thermally insulating end door for each of the first and second open ends, constituted by an assembly of methyl polymethacrylate panels separated by interstitial air, and thermally-insulating and gas-tight means between said doors and said cylinder;

said heating means comprising a first electrically resistive metallic wire helically wound on the external periphery of said cylinder.

2. A device according to claim 1, wherein said heating means are controlled and comprise a temperature transducer element in the form of a second electrically resistive metallic wire helically wound on said external periphery of said cylinder parallel to said first electrically resistive metallic wire.

3. A device according to claim 1, wherein said means for creating in said chamber an atmosphere of air of predetermined humidity, said means for causing said combustion of a sample of material in said chamber, said water circulation cooling means for condensing said smoke and products of pyrolysis generated by said combustion on said electrically resistive metallic element, and said electrically resistive metallic element are mounted on said doors of said chamber.

* * * * *

UNITED STATES PATENT OFFICE
CERTIFICATE OF CORRECTION

Patent No. 4,789,524          Dated December 6, 1988

Inventor(s) Pierre Rio et al.

It is certified that error appears in the above-identified patent and that said Letters Patent is hereby corrected as shown below:

In the Abstract, line 3, delete "humitidy" and insert
-- humidity --

Column 1, line 38, delete "nn" and insert -- in --

Column 5, line 3, delete "determined" and insert
-- predetermined --

Signed and Sealed this

Sixth Day of June, 1989

*Attest:*

DONALD J. QUIGG

*Attesting Officer*          *Commissioner of Patents and Trademarks*